United States Patent
Amplatz

(10) Patent No.: US 6,368,339 B1
(45) Date of Patent: *Apr. 9, 2002

(54) METHOD OF FORMING MEDICAL DEVICES: INTRA-VASCULAR OCCLUSION DEVICES

(75) Inventor: Curtis Amplatz, St. Paul, MN (US)

(73) Assignee: AGA Medical Corporation, Golden Valley, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/574,974

(22) Filed: May 19, 2000

Related U.S. Application Data

(62) Division of application No. 08/272,335, filed on Jul. 8, 1994, now Pat. No. 6,123,715.

(51) Int. Cl.$^7$ .............................................. A61M 29/00
(52) U.S. Cl. ........................ 606/200; 623/1.2; 606/213
(58) Field of Search ........................... 606/1, 151, 200, 606/198, 108, 213; 623/1.11, 1.1, 1.12–2.42, 11.11, 900, 901

(56) References Cited

U.S. PATENT DOCUMENTS

| | | |
|---|---|---|
| 3,334,629 A | 8/1967 | Cohn |
| 3,540,431 A | 11/1970 | Mobin-Uddin |
| 3,868,956 A | 3/1975 | Alfidi et al. |

(List continued on next page.)

FOREIGN PATENT DOCUMENTS

| | | |
|---|---|---|
| AU | 489252 | 12/1977 |
| DE | 2 821 048 | 5/1978 |
| DE | 233 303 A1 | 2/1986 |
| EP | 0 547530 A1 | 12/1992 |
| EP | 0541063 | 12/1993 |
| FR | 2 641 692 | 7/1990 |
| GB | 2 020 557 | 11/1979 |
| SU | 1468511 A1 | 3/1989 |
| WO | WO 93/10714 | 6/1993 |
| WO | 93/13712 | 7/1993 |
| WO | WO 96/01591 | 1/1996 |

OTHER PUBLICATIONS

"When Hope is All in Vein" *Sweden Now*, 1988.
"Transluminally–placed Coilspring Endarterial Tube Grafts, Long–term Patency in Canine Popliteal Artery" Dotter, *Investigative Radiology*, vol. 4, Sep.–Oct., 1969: 329–332.
Migration of a Kimray–Greenfield Filter to the Right Ventricle Castaneda, et al. *Radiology*, Dec. 1983, pp. 687–690.
Article entitled: Comparative In Vitro Evaluation of the Nitinol Inferior Vena Cava Filer Palestrant, et al. pp. 351–355.
"Catheter Closure of the Ductus Arteriosus" Lee Benson, M.D.F.R.C.P. (C.)–*Transcatheter Therapy in Pediatric Cardiology*–pp. 321–333.

(List continued on next page.)

*Primary Examiner*—Glenn K. Dawson
(74) *Attorney, Agent, or Firm*—Nikolai & Mersereau, P.A.

(57) ABSTRACT

The present invention provides a method of forming a medical device and medical devices which can be formed in accordance with the method. In one embodiment, the method includes the steps of a) providing a metal fabric formed of a plurality of strands formed of a metal which can be heat treated to substantially set a desired shape; b) deforming the metal fabric to generally conform to a surface of a molding element; c) heat treating the metal fabric in contact with the surface of the molding element to substantially set the shape of the fabric in its deformed state; and d) removing the metal fabric from contact with the molding element. The resulting metal fabric will define a medical device which can be collapsed for passage through a catheter or the like for deployment in a channel of a patient's body. Medical devices made in accordance with this method can have varying structures.

13 Claims, 11 Drawing Sheets

U.S. PATENT DOCUMENTS

| | | |
|---|---|---|
| 3,874,388 A | 4/1975 | King et al. |
| 3,952,747 A | 4/1976 | Kimmell, Jr. |
| 3,996,938 A | 12/1976 | Clark, III |
| 4,007,743 A | 2/1977 | Blake |
| 4,425,908 A | 1/1984 | Simon |
| 4,494,531 A | 1/1985 | Gianturco |
| 4,503,569 A | 3/1985 | Dotter |
| 4,553,545 A | 11/1985 | Maass et al. |
| 4,572,186 A | 2/1986 | Gould et al. |
| 4,619,246 A | 10/1986 | Molgaard-Nielsen et al. |
| 4,619,346 A | 10/1986 | Deguerry |
| 4,643,184 A | 2/1987 | Mobin-Uddin |
| 4,649,922 A | 3/1987 | Wiktor |
| 4,650,466 A | 3/1987 | Luther |
| 4,655,771 A | 4/1987 | Wallsten |
| 4,655,772 A | 4/1987 | De Liotta et al. |
| 4,665,906 A | 5/1987 | Jervis |
| 4,681,110 A | 7/1987 | Wiktor |
| 4,690,684 A | 9/1987 | McGreevy et al. |
| 4,699,611 A | 10/1987 | Bowden |
| 4,723,549 A | 2/1988 | Wholey et al. |
| 4,727,873 A | 3/1988 | Mobin-Uddin |
| 4,732,152 A | 3/1988 | Wallsten et al. |
| 4,732,153 A | 3/1988 | Phillips |
| 4,733,665 A | 3/1988 | Palmaz |
| 4,793,348 A | 12/1988 | Palmaz |
| 4,794,928 A | 1/1989 | Kletschka |
| 4,800,882 A | 1/1989 | Gianturco |
| 4,817,600 A | 4/1989 | Herms et al. |
| 4,830,003 A | 5/1989 | Wolff et al. |
| 4,832,055 A | 5/1989 | Palestrant |
| 4,836,204 A | 6/1989 | Landymore et al. |
| 4,848,343 A | 7/1989 | Wallsten et al. |
| 4,856,516 A | 8/1989 | Hillstead |
| 4,873,978 A | 10/1989 | Ginsburg |
| 4,886,062 A | 12/1989 | Wiktor |
| 4,917,089 A | 4/1990 | Sideris |
| 4,921,484 A | 5/1990 | Hillstead |
| 4,935,068 A | 6/1990 | Duerig |
| 4,969,891 A | 11/1990 | Gewertz |
| 4,984,581 A | 1/1991 | Stice |
| 4,990,156 A | 2/1991 | Lefebvre |
| 4,991,602 A | 2/1991 | Amplatz et al. |
| 4,998,539 A | 3/1991 | Delsanti |
| 5,002,560 A | 3/1991 | Machold et al. |
| 5,016,808 A | 5/1991 | Heil, Jr. et al. |
| 5,026,377 A | 6/1991 | Burton et al. |
| 5,034,001 A | 7/1991 | Garrison et al. |
| 5,041,093 A | 8/1991 | Chu |
| 5,053,008 A | 10/1991 | Bajaj |
| 5,059,205 A | 10/1991 | El-Nounou et al. |
| 5,064,435 A | 11/1991 | Porter |
| 5,067,489 A | 11/1991 | Lind |
| 5,067,957 A | 11/1991 | Jervis |
| 5,098,776 A | 3/1992 | Kobayashi et al. |
| 5,108,418 A | 4/1992 | Lefebvre |
| 5,108,419 A | 4/1992 | Reger et al. |
| 5,108,420 A | 4/1992 | Marks |
| 5,133,733 A | 7/1992 | Rasmussen et al. |
| 5,152,777 A | 10/1992 | Goldberg et al. |
| 5,171,259 A | 12/1992 | Inoue |
| 5,190,536 A | 3/1993 | Wood et al. |
| 5,190,546 A | 3/1993 | Jervis |
| 5,192,301 A | 3/1993 | Kamiya et al. |
| 5,221,261 A | 6/1993 | Termin et al. |
| 5,246,445 A | 9/1993 | Yachia et al. |
| 5,256,146 A | 10/1993 | Ensminger et al. |
| 5,334,217 A | 8/1994 | Das |
| 5,354,310 A | 10/1994 | Garnic et al. |
| 5,382,259 A | 1/1995 | Phelps et al. |
| 5,383,892 A | 1/1995 | Cardon et al. |
| 5,417,708 A | 5/1995 | Hall et al. |
| 5,421,955 A | 6/1995 | Lau et al. |
| 5,451,235 A | 9/1995 | Lock et al. |
| 5,456,693 A | 10/1995 | Conston et al. |
| 5,466,242 A | 11/1995 | Mori |
| 5,496,277 A | 3/1996 | Termin et al. |
| 5,496,332 A | 3/1996 | Sierra et al. |
| 5,514,115 A | 5/1996 | Frantzen et al. |
| 5,522,822 A | 6/1996 | Phelps et al. |
| 5,527,338 A | 6/1996 | Purdy |
| 5,545,208 A | 8/1996 | Wolff et al. |
| 5,597,378 A | 1/1997 | Jervis |
| 5,634,936 A | 6/1997 | Linden et al. |
| 5,645,558 A | 7/1997 | Horton |
| 5,690,671 A | 11/1997 | McGurk et al. |
| 5,702,421 A | 12/1997 | Schneidt |
| 5,709,707 A | 1/1998 | Lock et al. |
| 5,725,552 A | 3/1998 | Kotula et al. |
| 5,733,294 A | 3/1998 | Forber et al. |
| 6,123,715 A * | 9/2000 | Amplatz .................... 606/200 |

OTHER PUBLICATIONS

"Transcatheter Closure of Atrial Septal Defects" Larry A. Latson, M.D. *Transcatheter Therapy in Pediatric Cardiology*–pp. 335–348.

Transcatheter Closure of Heart Defects: Role of "Buttoned" Devices P. Syamasundar Rao,, M.D. and E.B. Sideris, M.D. *Transcatheter Therapy in Pediatric Cardiology*–pp. 349–369.

Superelastic Nitinol for Medical Devices Duerig, *Medical Plastics and Biomaterials*, vol. 4, No. 2, Mar./Apr. 1997 pp. 30–43.

"Atherosclerotic Rabbit Aortas: Expandable Intraluminal Grafting" Palmaz, et al. *Radiology 1986*; 160: 723–726.

"Self–expanding Endovascular Prothesis: An Experimental Study" Rosseau, et al. *Radiology 1987*; 164: 709–714.

Self–expanding Metallic Stents for Small Vessels: An Experimental Study Duprat, Jr. et al. *Radiology 1987*; 162: 469–472.

"Transluminal Expandable Nitinol Coil Stent Grafting: Preliminary Report" Dotter, et al. *Radiology 147*; 259–260 Apr. 1983.

"Balloon–expandable Intracoronary Stents in the Adult Dog" Schatz, et al. *Circulation*, vol. 76, No. 2, Aug. 1987; 450–457.

* cited by examiner

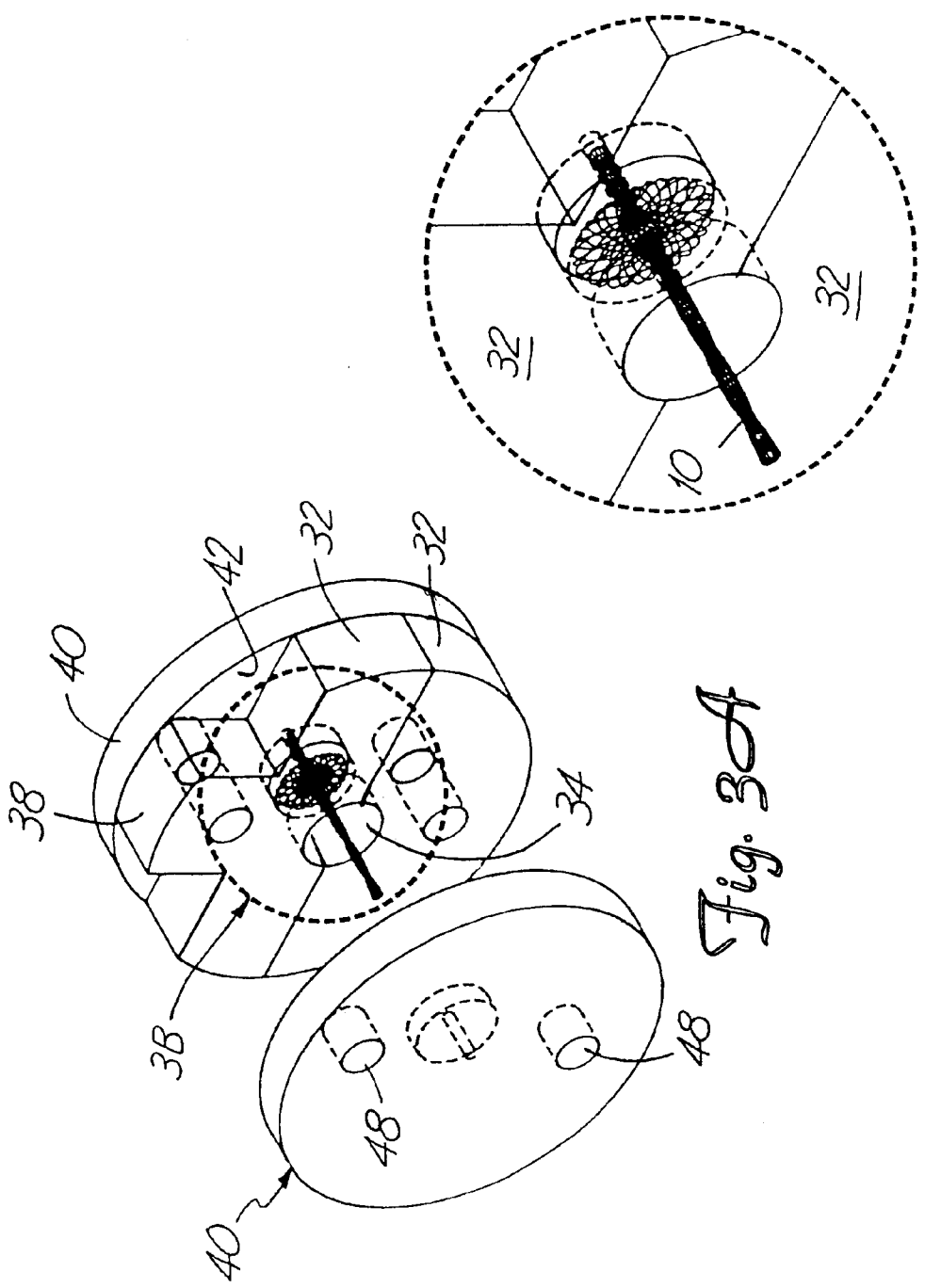

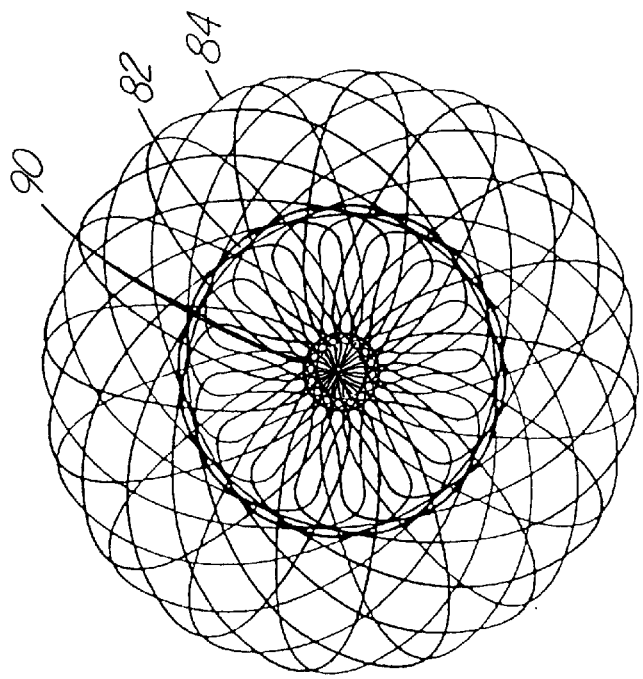
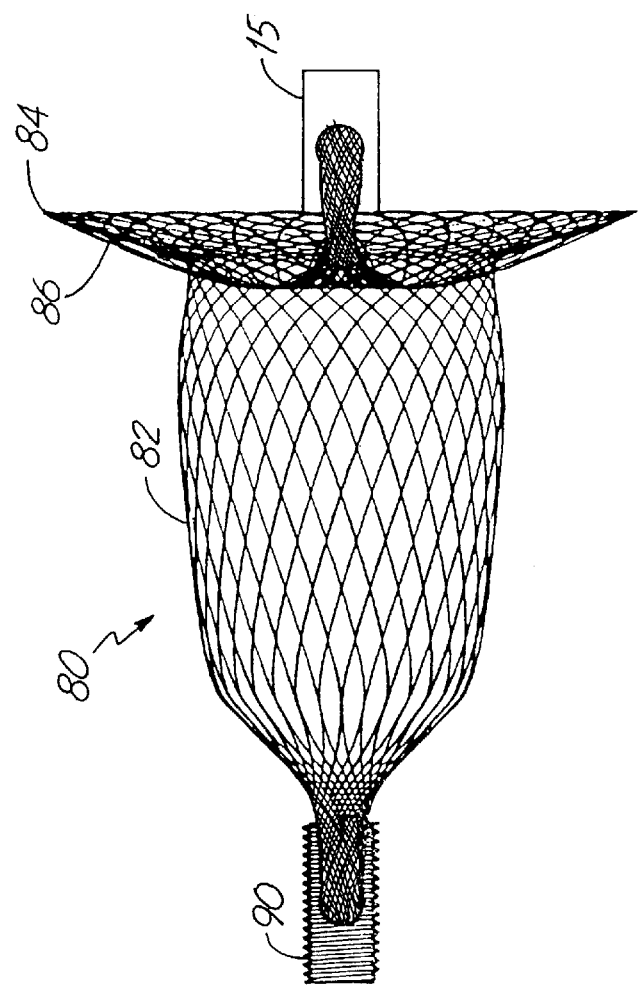

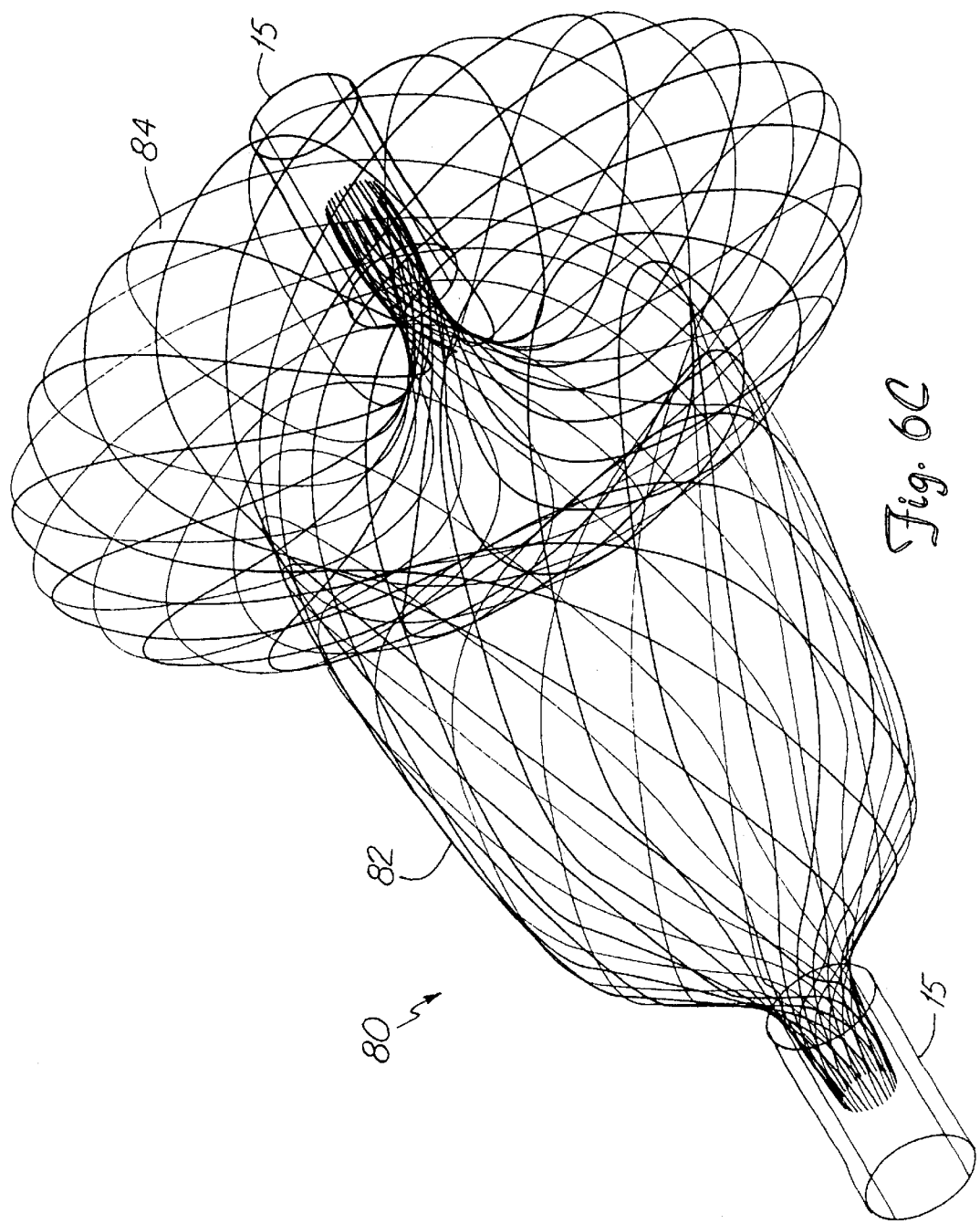

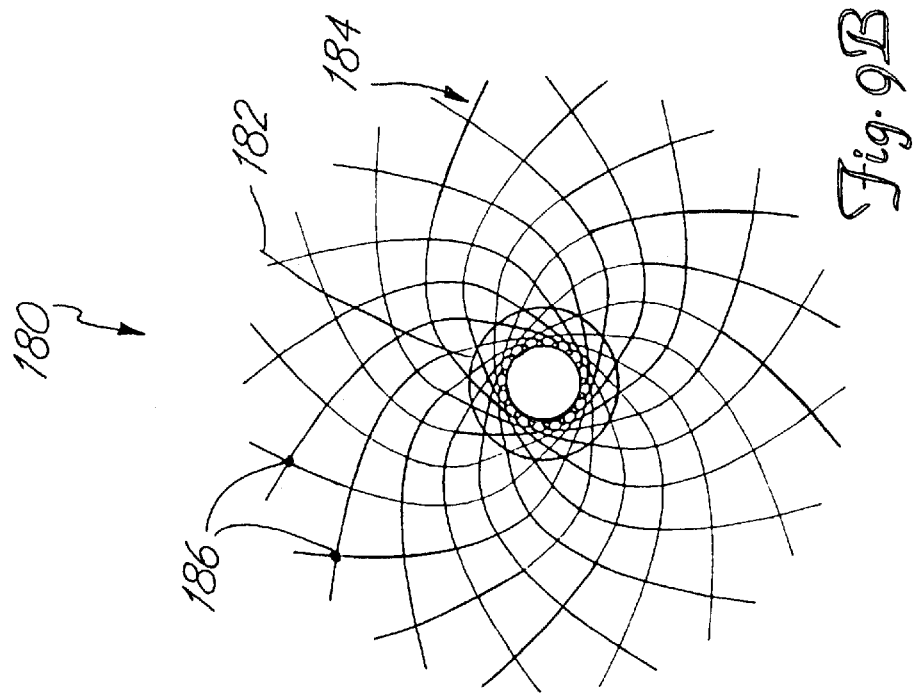
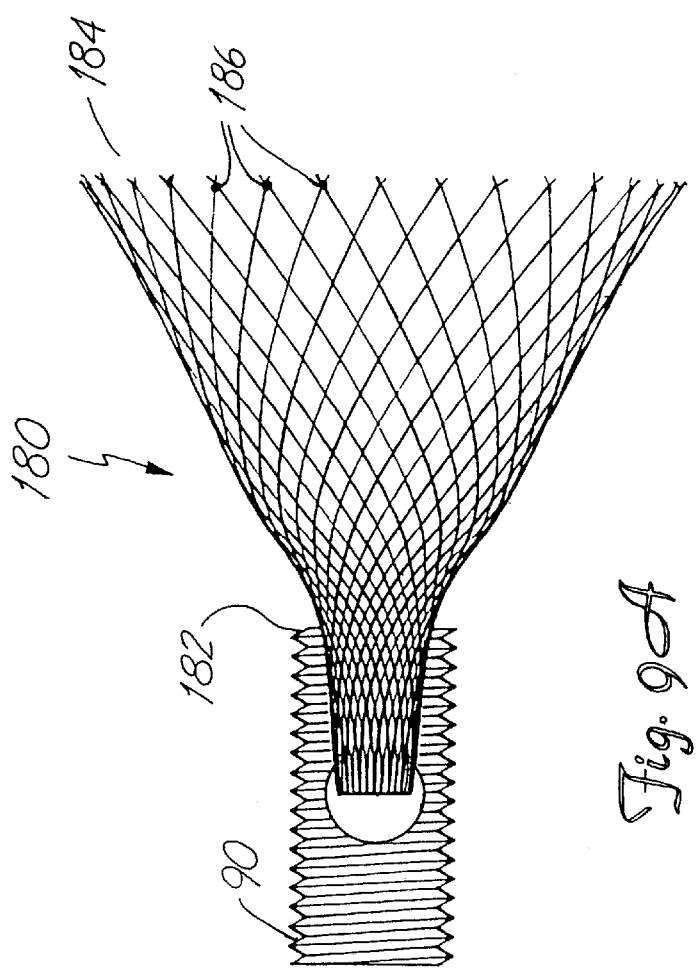

METHOD OF FORMING MEDICAL DEVICES: INTRA-VASCULAR OCCLUSION DEVICES

This is a divisional of application Ser. No. 08/272,335, filed on Jul. 8, 1994, now U.S. Pat. No. 6,123,715.

FIELD OF THE INVENTION

The present invention generally relates to intravascular devices for treating certain medical conditions and, more particularly, provides a method of forming intravascular devices and certain novel intravascular occlusion devices. The devices made in accordance with the invention are particularly well suited for delivery through a catheter or the like to a remote location in a patient's vascular system or in analogous vessels within a patient's body.

BACKGROUND OF THE INVENTION

A wide variety of intravascular devices are used in various medical procedures. Certain intravascular devices, such as catheters and guidewires, are generally used simply to deliver fluids or other medical devices to specific locations within a patient's body, such as a selective site within the vascular system. Other, frequently more complex, devices are used in treating specific conditions, such as devices used in removing vascular occlusions or for treating septal defects and the like.

In certain circumstances, it may be necessary to occlude a patient's vessel, such as to stop blood flow through an artery to a tumor or other lesion. Presently, this is commonly accomplished simply by inserting, e.g. Ivalon particles, a trade name for vascular occlusion particles, and short sections of coil springs into a vessel at a desired location. These "embolization agents" will eventually become lodged in the vessel, frequently floating downstream of the site at which they are released before blocking the vessel. In part due to the inability to precisely position the embolization agents, this procedure is often limited in its utility.

Detachable balloon catheters are also used to block patients' vessels. When using such a catheter, an expandable balloon is carried on a distal end of a catheter. When the catheter is guided to the desired location, the balloon is filled with a fluid until it substantially fills the vessel and becomes lodged therein. Resins which will harden inside the balloon, such as an acrylonitrile, can be employed to permanently fix the size and shape of the balloon. The balloon can then be detached from the end of the catheter and left in place.

Such balloon embolizations are also prone to certain safety problems, though. For example, if the balloon is not filled enough, it will not be firmly fixed in the vessel and may drift downstream within the vessel to another location, much like the loose embolization agents noted above. In order to avoid this problem, physicians may overfill the balloons; it is not uncommon for balloons to rupture and release the resin into the patient's bloodstream.

Mechanical embolization devices, filters and traps have been proposed in the past. Even if some of those devices have proven effective, they tend to be rather expensive and time-consuming to manufacture. For example, some intravascular blood filters suggested by others are formed of a plurality of specially-shaped legs which are adapted to fill the vessel and dig into the vessel walls. In making most such filters, the legs must be individually formed and then painstakingly attached to one another, frequently entirely by hand, to assemble the final filter. Not only does this take significant skilled manpower, and hence increase the costs of such devices, the fact that each item must be made by hand tends to make quality control more difficult. This same difficulty and expense of manufacturing is not limited to such filters, but is experienced in many other intravascular devices as well.

Accordingly, it would be desirable to provide a method for forming devices for deployment in a vessel in a patient's body which is both economical and yields consistent, reproducible results. It would also be advantageous to provide a reliable embolization device which is both easy to deploy and can be accurately placed in a vessel.

SUMMARY OF THE INVENTION

The present invention provides a method for forming intravascular devices from a resilient metal fabric and medical devices which can be formed in accordance with this method. In the method of the invention, a metal fabric formed of a plurality of resilient strands is provided, with the wires being formed of a resilient material which can be heat treated to substantially set a desired shape. This fabric is then deformed to generally conform to a molding surface of a molding element and the fabric is heat treated in contact with the surface of the molding element at an elevated temperature. The time and temperature of the heat treatment is selected to substantially set the fabric in its deformed state. After the heat treatment, the fabric is removed from contact with the molding element and will substantially retain its shape in the deformed state. The fabric so treated defines an expanded state of a medical device which can be deployed through a catheter into a channel in a patient's body.

In accordance with the method of the invention, a distal end of a catheter can be positioned in a channel in a patient's body to position the distal end of the catheter adjacent a treatment site for treating a physiological condition. A medical device made in accordance with the process outlined above can be collapsed and inserted into the lumen of the catheter. The device is urged through the catheter and out the distal end, whereupon it will tend to return to its expanded state adjacent the treatment site.

Further embodiments of the present invention also provide specific medical devices which may be made in accordance with the present invention. Such devices of the invention are formed of a metal fabric and have an expanded configuration and a collapsed configuration. The devices are collapsed for deployment through a catheter and, upon exiting the distal end of the catheter in a patient's channel, will resiliently substantially return to their expanded configuration. In accordance with a first of these embodiments, a generally elongate medical device has a generally tubular middle portion and a pair of expanded diameter portions, with one expanded diameter portion positioned at either end of the middle portion. In another embodiment, the medical device is generally bell-shaped, having an elongate body having a tapered first end and a larger second end, the second end presenting a fabric disc which will be oriented generally perpendicular to an axis of a channel when deployed therein.

BRIEF DESCRIPTION OF THE DRAWINGS

FIG. 3A is a perspective view showing the molding element and metal fabric of FIG. 2 in a partially assembled state;

FIG. 3B is a close-up view of the highlighted area of FIG. 3A showing the compression of the metal fabric in the molding element;

FIGS. 6A–6C are a side view, an end view and a perspective view, respectively, of a medical device in accordance with another embodiment of the invention;

FIGS. 9A and 9B are a side view and an end view, respectively, of a medical device in accordance with yet another embodiment of the invention:

DETAILED DESCRIPTION OF THE PREFERRED EMBODIMENTS

Figure 1B:
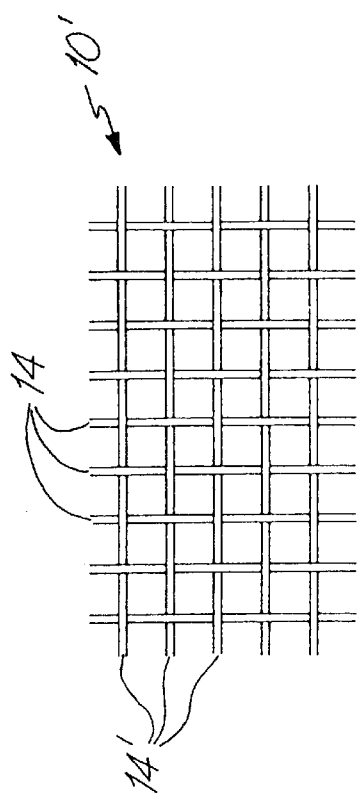
FIGS. 1A and 1B each depict a metal fabric suitable for use with the invention.
Figure 1A:
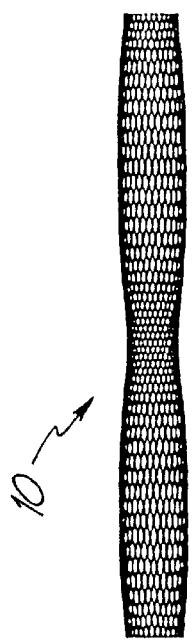

The present invention provides a reproducible, relatively inexpensive method of forming devices for use in channels in patients' bodies, such as vascular channels, urinary tracts, biliary ducts and the like, as well as devices which may be made via that method. In forming a medical device via the method of the invention, a metal fabric 10 is provided. The fabric is formed of a plurality of wire strands having a predetermined relative orientation between the strands. FIGS. 1A and 1B illustrate two examples of metal fabrics which are suitable for use in the method of the invention.

In the fabric of FIG. 1A, the metal strands define two sets of essentially parallel generally helical strands, with the strands of one set having a "hand", i.e. a direction of rotation, opposite that of the other set. This defines a generally tubular fabric, known in the fabric industry as a tubular braid. Such tubular braids are well known in the fabric arts and find some applications in the medical device field as tubular fabrics, such as in reinforcing the wall of a guiding catheter. As such braids are well known, they need not be discussed at length here.

The pitch of the wire strands (i.e. the angle defined between the turns of the wire and the axis of the braid) and the pick of the fabric (i.e. the number of turns per unit length) may be adjusted as desired for a particular application. For example, if the medical device is to be formed is to be used to occlude the channel in which it is placed, the pitch and pick of the fabric will tend to be higher than if the device is simply intended to filter bodily fluid passing therethrough.

For example, in using a tubular braid such as that shown in FIG. 1A to form a device such as that illustrated in FIGS. 5A and 5B, a tubular braid of about 4 mm in diameter with a pitch of about 50° and a pick of about 74 (per linear inch) would seem suitable for a devices used in occluding channels on the order of about 2 mm to about 4 mm in inner diameter, as detailed below in connection with the embodiment of FIGS. 5A and 5B.

FIG. 1B illustrates another type of fabric which is suitable for use in the method of the invention. This fabric is a more conventional fabric and may take the form of a flat woven sheet, knitted sheet or the like. In the woven fabric shown in FIG. 1B, there are also two sets 14 and 14' of generally parallel strands, with one set of strands being oriented at an angle, e,g, generally perpendicular (having a pick of about 90°), with respect to the other set. As noted above, the pitch and pick of this fabric (or, in the case of a knit fabric, the pick and the pattern of the kit, e.g. Jersey or double knits) may be selected to optimize the desired properties of the final medical device.

The wire strands of the metal fabric used in the present method should be formed of a material which is both resilient and can be heat treated to substantially set a desired shape. Materials which are believed to be suitable for this purpose include a cobalt-based low thermal expansion alloy referred to in the field as Elgiloy, nickel-based high-temperature high-strength "superalloys" commercially available from Haynes International under the trade name Hastelloy, nickel-based heat treatable alloys sold under the name Incoloy by International Nickel, and a number of different grades of stainless steel. The important factor in choosing a suitable material for the wires is that the wires retain a suitable amount of the deformation induced by the molding surface (as described below) when subjected to a predetermined heat treatment.

One class of materials which meet these qualifications are so-called shape memory alloys. Such alloys tend to have a temperature induced phase change which will cause the material to have a preferred configuration which can be fixed by heating the material above a certain transition temperature to induce a change in the phase of the material. When the alloy is cooled back down, the alloy will "remember" the shape it was in during the heat treatment and will tend to assume that configuration unless constrained from so doing.

One particularly preferred shape memory alloy for use in the present method is nitinol, an approximately stoichiometric alloy of nickel and titanium, which may also include other minor amounts of other metals to achieve desired properties. NiTi alloys such as nitinol, including appropriate compositions and handling requirements, are well known in the art and such alloys need not be discussed in detail here. For example, U.S. Pat. No. 5,067,489 (Lind) and U.S. Pat. No. 4,991,602 (Amplatz et al.), the teachings of which are incorporated herein by reference, discuss the use of shape memory NiTi alloys in guidewires. Such NiTi alloys are preferred, at least in part, because they are commercially available and more is known about handling such alloys than other known shape memory alloys. NiTi alloys are also very elastic—they are said to be "superelastic" or "pseudoelastic". This elasticity will help a device of the invention return to a present expanded configuration for deployment.

The wire strands can comprise a standard monofilament of the selected material, i.e. a standard wire stock may be used. If so desired, though, the individual wire strands may be formed from "cables" made up of a plurality of individual wires. For example, cables formed of metal wires where several wires are helically wrapped about a central wire are commercially available and NiTi cables having an outer diameter of 0.003 inches or less can be purchased. One advantage of certain cables is that they tend to be "softer" than monofilament wires having the same diameter and formed of the same material. Additionally, if the device being formed from the wire strands is to be used to occlude a vessel, the use of a cable can increase the effective surface area of the wire strand, which will tend to promote thrombosis.

In preparation of forming a medical device in keeping with the invention, an appropriately Sized piece of the metal fabric is cut from the larger piece of fabric which is formed, for example, by braiding wire strands to form a long tubular braid. The dimensions of the piece of fabric to be cut will depend, in large part, upon the size and shape of the medical device to be formed therefrom.

When cutting the fabric to the desired dimensions, care should be taken to ensure that the fabric will not unravel. In the case of tubular braids formed of NiTi alloys, for example, the individual wire strands will tend to return to their heat-set configuration unless constrained. If the braid is heat treated to set the strands in the braided configuration, they will tend to remain in the braided form and only the ends will become frayed. However, it may be more economical to simply form the braid without heat treating the braid since the fabric will be heat treated again in forming the medical device, as noted below.

In such untreated NiTi fabrics, the strands will tend to return to their unbraided configuration and the braid can unravel fairly quickly unless the ends of the length of braid cut to form the device are constrained relative to one another. One method which has proven to be useful to prevent the braid from unraveling is to clamp the braid at two locations and cut the braid to leave a length of the braid having clamps (15 in FIG. 2) at either end, thereby effectively defining an empty space within a sealed length of fabric. These clamps 15 will hold the ends of the cut braid together and prevent the braid from unraveling.

Alternatively, one can solder, braze, weld or otherwise affix the ends of the desired length together (e.g. with a biocompatible cementitious organic material) before cutting the braid. Although soldering and brazing of NiTi alloys has proven to be fairly difficult, the ends can be welded together, such as by spot welding with a laser welder.

The same problems present themselves when a flat sheet of fabric such as the woven fabric shown in FIG. 1B is used. With such a fabric, the fabric can be inverted upon itself to form a recess or depression and the fabric can be clamped about this recess to form an empty pocket (not shown) before the fabric is cut. If it is desired to keep the fabric in a generally flat configuration, it may be necessary to weld the junctions of the strands together adjacent the periphery of the desired piece of fabric before that piece is cut from the larger sheet. So connecting the ends of the strands together will prevent fabrics formed of untreated shape memory alloys and the like from unraveling during the forming process.

Once an appropriately sized piece of the metal fabric is obtained, the fabric is deformed to generally conform to a surface of a molding element. As will be appreciated more fully from the discussion below in connection with FIGS. 2–10, so deforming the fabric will reorient the relative positions of the strands of the metal fabric from their initial order to a second, reoriented configuration. The shape of the molding element should be selected to deform the fabric into substantially the shape of the desired medical device.

The molding element can be a single piece, or it can be formed of a series of mold pieces which together define the surface to which the fabric will generally conform. The molding element can be positioned within a space enclosed by the fabric or can be external of such a space, or can even be both inside and outside such a space.

Figure 2B:
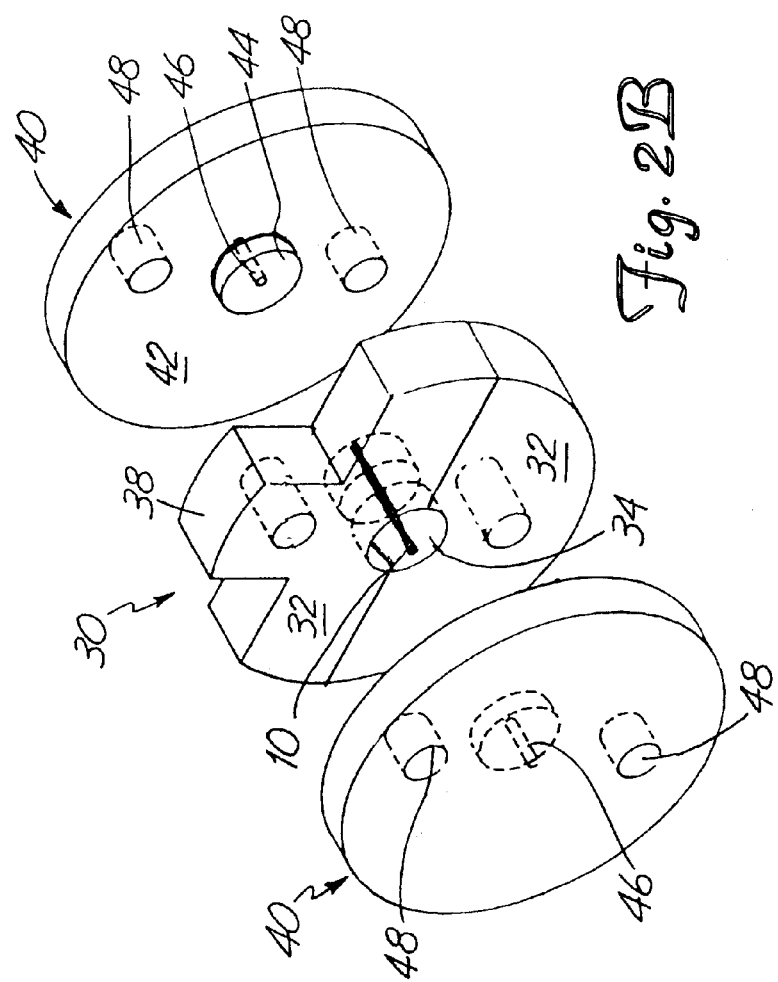
FIGS. 2A and 2B are a side view and a perspective view, respectively, of a molding element and a length of a metal fabric suitable for use in forming a medical device in accordance with the invention, the mold being in a disassembled state.
Figure 2A:
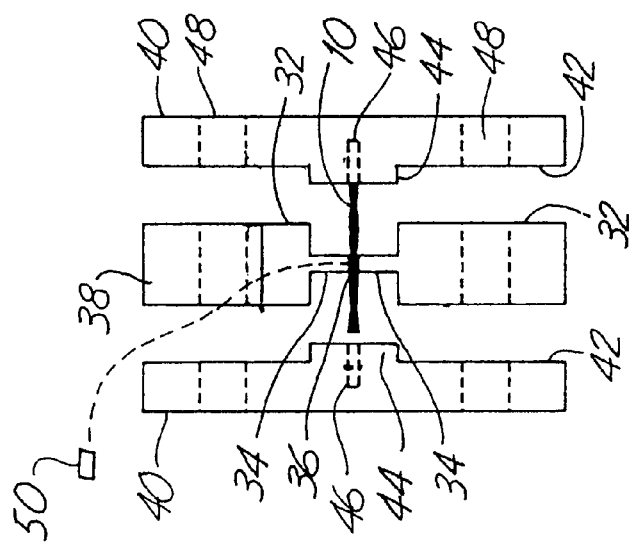
Figure 4:
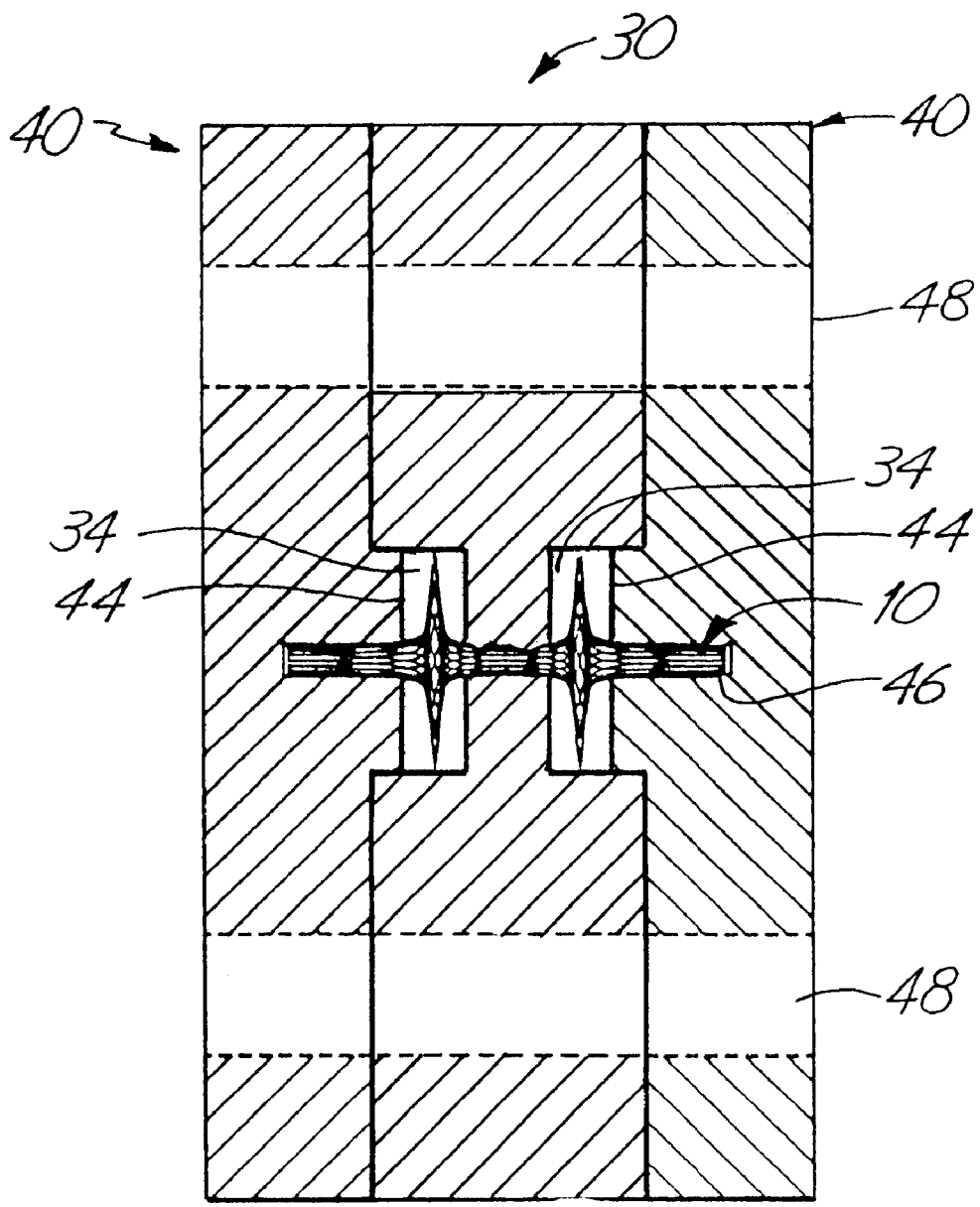
FIG. 4 is a cross-sectional view showing the molding element and metal fabric of FIG. 2 in an assembled state.

In order to illustrate one example of how such a mold may be configured and how it may be used in accordance with the method of the invention, reference will be had to FIGS. 2–5. In FIGS. 2–4, the molding element 20 is formed of a number of separate pieces which can be attached to one another to complete the molding element 20. In using such a multi-piece molding element, the mold can be assembled about the cut length of fabric 10, thereby deforming the fabric to generally conform to the desired surface (or surfaces) of the molding element.

In the molding element illustrated in FIGS. 2–4, the metal fabric 10 is deformed to generally conform to a surface of the molding element 20, the molding element comprising a center section 30 and a pair of end plates 40. Turning first to the center section 30, the center section is desirably formed of opposed halves 32, 32 which can be moved away from one another in order to introduce the metal fabric 10 into the mold. Although these two halves 32, 32 are shown in the drawings as being completely separated from one another, it is to be understood that these halves could be interconnected, such as by means of a hinge or the like, if so desired. The opposed halves of the molding element shown in the drawings of FIGS. 2 and 3 each include a pair of semi-circular recesses opposed on either side of a ridge defining a generally semi-circular opening. When the two halves are assembled in forming the device, as best seen in FIG. 3, the semi-circular openings in the opposed halves 32, 32 mate to define a generally circular forming port 36 passing through the center section 30. Similarly, the semi-circular recesses in the two halves together form a pair of generally circular central recesses 34, with one such recess being disposed on either face of the center section.

The overall shape and dimensions of the center section can be varied as desired; it is generally the size of the central recesses 34 and the forming port 36 which will define the size and shape of the middle of the finished device, as explained below. If so desired, each half 32 may be provided with a manually graspable projection 38. In the embodiment shown in the drawings, this projection 38 is provided at a location disposed away from the abutting faces of the respective halves. Such a manually graspable projection 38 will simply enable an operator to more easily join the two halves to define the recesses 34 and forming port 36.

The center section is adapted to cooperatively engage a pair of end plates 40 for forming the desired device. In the embodiment shown in FIGS. 2 and 3, the center section 30 has a pair of flat outer faces 39 which are each adapted to be engaged by an inner face 42 of one of the two end plates 40. Each end plate includes a compression disk 44 which extends generally laterally inwardly from the inner face 42 of the end plate. This compression disk 44 should be sized to permit it to be received within one of the central recesses 34 on either face of the center section 30. For reasons explained more fully below, each compression disk 44 includes a cavity 46 for receiving an end of the length of the metal fabric 10.

One or more channels 48 for receiving bolts and the like may also be provided through each of the end plates and through the center section 30. By passing bolts through these channels 48, one can assemble the molding element 20 and retain the metal fabric in the desired shape during the heat treatment process, as outlined below.

In utilizing the molding element 20 shown in FIGS. 2–4, a length of the metal fabric 10 can be positioned between the opposed halves 32 of the center section 30. In the drawings of the molding element 20 of FIGS. 2–4, the metal fabric 10 is a tubular braid such as that illustrated in FIG. 1A. A sufficient length of the tubular braid should be provided to permit the fabric to conform to the molding surface, as explained below. Also, as noted above, care should be taken to secure the ends of the wire strands defining the tubular braid in order to prevent the metal fabric from unraveling.

A central portion of the length of the metal braid may be positioned within one of the two halves of the forming port 36 and the opposed halves 32 of the center section may be joined to abut one another to restrain a central portion of the metal braid within the central forming port 36 through the center section.

The tubular braid will tend to have a natural, relaxed diameter which is defined, in large part, when the tubular braid is formed. Unless the tubular braid is otherwise deformed, when the wire strands are in their relaxed state they will tend to define a generally hollow tube having the predetermined diameter. The outer diameter of the relaxed braid may be, for example, about 4 mm. The relative size of the forming port 36 in the central section 30 of the molding element and the natural, relaxed outer diameter of the tubular braid may be varied as desired to achieve the desired shape of the medical device being formed.

In the embodiment shown in FIGS. 2 and 3, the inner diameter of the forming port 36 is optimally slightly less than the natural, relaxed outer diameter of the tubular braid 10. Hence, when the two halves 32, 32 are assembled to form the center section 30, the tubular braid 10 will be slightly compressed within the forming port 36. This will help ensure that the tubular braid conforms to the inner surface of the forming port 36, which defines a portion of the molding surface of the molding element 20.

If so desired, a generally cylindrical internal molding section (not shown) may also be provided. This internal molding section has a slightly smaller diameter than the inner diameter of the forming port 36. In use, the internal molding section is placed within the length of the metal fabric, such as by manually moving the wire strands of the fabric apart to form an opening through which the internal molding section can be passed. This internal molding section should be positioned within the tubular braid at a location where it will be disposed within the forming port 36 of the center section when the molding element is assembled. There should be a sufficient space between the outer surface of the interior molding section and the inner surface of the forming port 36 to permit the wire strands of the fabric 10 to be received therebetween.

By using such an internal molding section, the dimensions of the central portion of the finished medical device can be fairly accurately controlled. Such an internal molding section may be necessary in circumstances where the natural, relaxed outer diameter of the tubular braid 10 is less than the inner diameter of the forming port 36 to ensure that the braid conforms to the inner surface of that forming port. However, it is not believed that such an internal molding section would be necessary if the natural, relaxed outer diameter of the braid were larger than the inner diameter of the forming port 36.

As noted above, the ends of the tubular braid should be secured in order to prevent the braid from unraveling. Each end of the metal fabric 10 is desirably received within a cavity 46 formed in one of the two end plates 40. If a clamp (15 in FIG. 2) is used, the clamp may be sized to be relatively snugly received within one of these cavities 46 in order to effectively attach the end of the fabric to the end plate 40. The end plates can then be urged toward the center section 30 and toward one another until the compression disk 44 of each end plate is received within a central recess 34 of the center section 30. The molding element may then be clamped in position by passing bolts or the like through the channels 48 in the molding element and locking the various components of the molding element together by tightening a nut down onto such a bolt (not shown).

As best seen in FIG. 3A, when an end plate is urged toward the center section 30, this will compress the tubular braid 10 generally along its axis. When the tubular braid is in its relaxed configuration, as illustrated in FIG. 1A, the wire strands forming the tubular braid will have a first, predetermined relative orientation with respect to one another. As the tubular braid is compressed along its axis, the fabric will tend to flare out away from the axis, as illustrated in FIG. 4. When the fabric is so deformed, the relative orientation of the wire strands of the metal fabric will change. When the molding element is finally assembled, the metal fabric will generally conform to the molding surface of this element.

In the molding element 20 shown in FIGS. 2–4, the molding surface is defined by the inner surface of the forming port, the inner surfaces of the central recess 34 and the faces of the compression disks 44 which are received within the recesses 34. If an internal molding section is used, the cylindrical outer surface of that section may also be considered a part of the molding surface of the molding element 20. Accordingly, when the molding element 20 is completely assembled the metal fabric will tend to assume a somewhat "dumbbell"-shaped configuration, with a relatively narrow center section disposed between a pair of bulbous, perhaps even disk-shaped end sections, as best seen in FIG. 4.

It should be understood that the specific shape of the particular molding element 20 shown in FIGS. 2–4 is intended to produce one useful medical device in accordance with the present method, but that other molding elements having different configurations could also be used. If a more complex shape is desired, the molding element may have more parts, but if a simpler shape is being formed the molding element may have even fewer parts. The number of parts in a given molding element and the shapes of those parts will be dictated almost entirely by the shape of the desired medical device as the molding element must define a molding surface to which the metal fabric will generally conform.

Accordingly, the specific molding element 20 shown in FIGS. 2–4 is simply intended as one specific example of a suitable molding element for forming one particular useful medical device. Additional molding elements having different designs for producing different medical devices are explained below in connection with, e.g., FIGS. 8 and 10. Depending on the desired shape of the medical device being formed, the shape and configuration of other specific molding elements can be readily designed by those of ordinary skill in the art.

Once the molding element 20 is assembled with the metal fabric generally conforming to a molding surface of that element, the fabric can be subjected to a heat treatment while it remains in contact with that molding surface. This heat treatment will depend in large part upon the material of which the wire strands of the metal fabric are formed, but the time and temperature of the heat treatment should be selected to substantially set the fabric in its deformed state, i.e., wherein the wire strands are in their reoriented relative configuration and the fabric generally conforms to the molding surface.

The time and temperature of the heat treatment can vary greatly depending upon the material used in forming the wire strands. As noted above, one preferred class of materials for forming the wire stands are shape memory alloys, with nitinol, a nickel titanium alloy, being particularly preferred. If nitinol is used in making the wire strands of the fabric, the wire strands will tend to be very elastic when the metal is in its austenitic phase; this very elastic phase is frequently referred to as a "superelastic" or "pseudoelastic" phase. By heating the nitinol above a certain phase transition temperature, the crystal structure of the nitinol metal when in its austenitic phase can be set. This will tend to "set" the shape of the fabric and the relative configuration of the wire strands in the positions in which they are held during the heat treatment.

Suitable heat treatments of nitinol wire to set a desired shape are well known in the art. Spirally wound nitinol coils, for example, are used in a number of medical applications, such as in forming the coils commonly carried around distal lengths of guidewires. A wide body of knowledge exists for forming nitinol in such medical devices, so there is no need to go into great detail here on the parameters of a heat treatment for the nitinol fabric preferred for use in the present invention.

Briefly, though, it has been found that holding a nitinol fabric at about 500° C. to about 550° C. for a period of about 1 to about 30 minutes, depending on the softness or harness of the device to be made, will tend to set the fabric in its deformed state, i.e. wherein it conforms to the molding surface of the molding element. At lower temperatures the heat treatment time will tend to be greater (e.g. about one hour at about 350° C.) and at higher temperatures the time will tend to be shorter (e.g. about 30 seconds at about 900° C.). These parameters can be varied as necessary to accommodate variations in the exact composition of the nitinol, prior heat treatment of the nitinol, the desired properties of the nitinol in the finished article, and other factors which will be well known to those skilled in this field.

Instead of relying on convection heating or the like, it is also known in the art to apply an electrical current to the nitinol to heat it. In the present invention, this can be accomplished by, for example, hooking electrodes to the clamps 15 carried at either end of the metal fabric illustrated in FIG. 5. The wire can then be heated by resistance heating of the wires in order to achieve the desired heat treatment, which will tend to eliminate the need to heat the entire molding element to the desired heat treating temperature in order to heat the metal fabric to the desired temperature.

After the heat treatment, the fabric is removed from contact with the molding element and will substantially retain its shape in a deformed state. When the molding element 20 illustrated in FIGS. 2–4 is used, the bolts (not shown) may be removed and the various parts of the molding element may be disassembled in essentially the reverse of the process of assembling the molding element. If an internal molding section is used, this molding section can be removed in much the same fashion that it is placed within the generally tubular metal fabric in assembling the molding element 20, as detailed above.

Figure 5B:
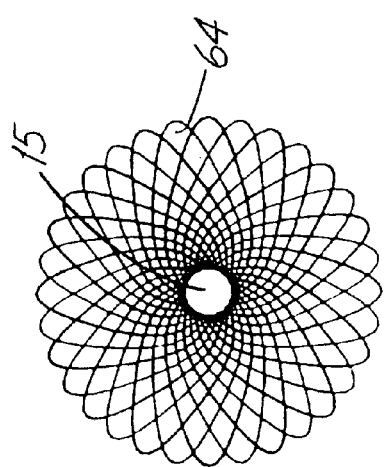
FIGS. 5A and 5B are a side view and an end view, respectively, of a medical device in accordance with the invention.
Figure 5A:
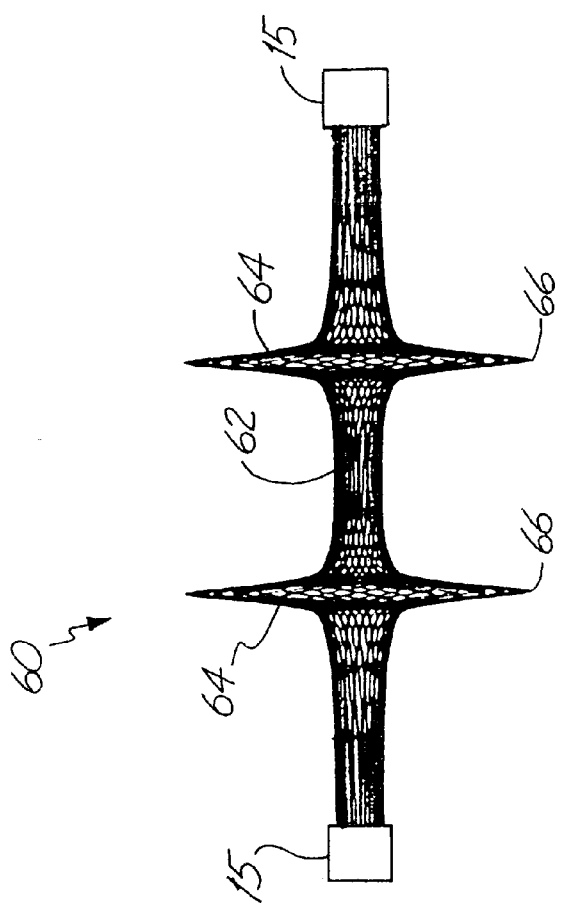

FIGS. 5A and 5B illustrate one embodiment of a medical device 60 which may be made using the molding element 20 of FIGS. 2–4. As discussed below, the device of FIG. 5 is particularly well suited for use in occluding a channel within a patient's body and these designs have particular advantages in use as vascular occlusion devices.

The vascular occlusion device 60 of FIG. 5A includes a generally tubular middle portion 62 and a pair of expanded diameter portions 64. One expanded diameter portion is disposed at either end of the generally tubular middle portion 62. In the embodiment shown in FIGS. 5A and 5B, the expanded diameter portions 64 include a ridge 66 positioned about midway along their lengths.

The relative sizes of the tubular middle section and the expanded diameter portions can be varied as desired. In this particular embodiment, the medical device is intended to be used as a vascular occlusion device to substantially stop the flow of blood through a patient's blood vessel. When the device 60 is deployed within a patient's blood vessel, as detailed below, it will be positioned within the vessel such that its axis generally coincides with the axis of the vessel. The dumbbell-shape of the present device is intended to limit the ability of the vascular occlusion device 60 to turn at an angle with respect to the axis of the blood vessel to ensure that it remains in substantially the same position in which the operator deploys it within the vessel.

Although the illustrated embodiments of this invention only have two expanded diameter portions, it should be understood that the device could have more than two such expanded diameter portions. For example, if the device has three expanded diameter portions, each expanded diameter portion is separated from at least one other expanded diameter portion by a tubular portion having a smaller diameter. If so desired, the diameters of each of the expanded diameter portions can be the same, but they need not be the same.

In order to relatively strongly engage the lumen of the blood vessel, the maximum diameter of the expanded diameter portions 64 (which occurs along the middle ridge 66 in this embodiment) should be selected so that it is at least as great as the diameter of the lumen of the vessel in which it is to be deployed, and is optimally slightly greater than that diameter. When it is deployed within the patient's vessel, the vascular occlusion device 60 will engage the lumen at two spaced-apart locations. The device 60 is desirably longer along its axis than the dimension of its greatest diameter. This will substantially prevent the vascular occlusion device 60 from turning within the lumen at an angle to its axis, essentially preventing the device from becoming dislodged and tumbling along the vessel with blood flowing through the vessel.

The relative sizes of the generally tubular middle portion 62 and expanded diameter portion 64 of the vascular occlusion device 60 can be varied as desired for any particular application. For example, the outer diameter of the middle portion 62 may range between about one quarter and about one third of the maximum diameter of the expanded diameter portions 64 and the length of the middle portion 62 may comprise about 20% to about 50% of the overall length of the device. Although these dimensions are suitable if the device 60 is to be used solely for occluding a vascular vessel, it is to be understood that these dimensions may be varied if the device is to be used in other applications, such as where the device is intended to be used simply as a vascular filter rather than to substantially occlude the entire vessel or where the device is deployed in a different channel in a patient's body.

The aspect ratio (i.e., the ratio of the length of the device over its maximum diameter or width) of the device 60 illustrated in FIGS. 5A and 5B is desirably at least about 1.0, with a range of about 1.0 to about 3.0 being preferred and an aspect ratio of about 2.0 being particularly preferred. Having a greater aspect ration will tend to prevent the device from rotating generally perpendicularly to its axis, which may be referred to as an end over end roll. So long as the outer diameter of the expanded diameter portions 64 of the device is large enough to seat the device fairly securely against the lumen of the channel in which the device is deployed, the inability of the device to turn end over end will help keep the device deployed precisely where it is positioned within the patient's vascular system or in any other channel in the patient's body. Alternatively, having expanded diameter portions which have natural, relaxed diameters substantially larger than the lumen of the vessels in which the device is deployed should also suffice to wedge the device into place in the vessel without undue concern being placed on the aspect ratio of the device.

The pick and pitch of the metal fabric 10 used in forming the device 60, as well as some other factors such as the number of wires employed in a tubular braid, are important in determining a number of the properties of the device. For example, the greater the pick and pitch of the fabric, and hence the greater the density of the wire strands in the fabric, the stiffer the device will be. Having a greater wire density will also provide the device with a greater wire surface area, which will generally enhance the tendency of the device to occlude a blood vessel in which it is deployed. This thrombogenicity can be either enhanced, e.g. by a coating of a thrombolytic agent or by attaching silk or wool fabric to the device, or abated, e.g. by a coating of a lubricious, anti-thrombogenic compound. A variety of materials and techniques for enhancing or reducing thrombogenicity are well known in the art and need not be detailed here.

When the device is deployed in a patient's vessel, thrombi will tend to collect on the surface of the wires. By having a greater wire density, the total surface area of the wires will be increased, increasing the thrombolytic activity of the device and permitting it to relatively rapidly occlude the vessel in which it is deployed. It is believed that forming the occlusion device 60 from a 4 mm diameter tubular braid having a pick of at least about 40 and a pitch of at least about 30° will provide sufficient surface area to substantially completely occlude a blood vessel of 2 mm to about 4 mm in inner diameter in a suitable period of time. If it is desired to increase the rate at which the device 60 occludes the vessel in which it is deployed, any of a wide variety of known thrombolytic agents can be applied to the device.

FIGS. 6A–6C illustrate an alternative embodiment of a medical device in accordance with the present invention. This device 80 has a generally bell-shaped body 82 and an outwardly extending forward end 84. One application for which this device is particularly well suited is occluding defects known in the art as patent ductus arteriosus (PDA). PDA is essentially a condition wherein two blood vessels, most commonly the aorta and pulmonary artery adjacent the heart, have a shunt between their lumens. Blood can flow directly between se two blood vessels through the shunt, compromising the normal flow of blood through the patient's vessels.

As explained more fully below in connection with FIG. 8, the bell-shaped body 82 is adapted to be deployed within the shunt between the vessels, while the forward end 84 Is adapted to be positioned within one of the two vessels to help seat the body in the shunt. The sizes of the body 82 and the end 84 can be varied as desired for differently sized shunts. For example, the body may have a diameter along its generally cylindrical middle 86 of about 10 mm and a length along it axis of about 25 mm. In such a device, the base 88 of the body may flare generally radially outward until it reaches an outer diameter equal to that of the forward end 84, which may be on the order of about 20 mm in diameter.

The base 88 desirably flares out relatively rapidly to define a shoulder tapering radially outwardly from the middle 86 of the body. When the device is deployed in a vessel, this shoulder will abut the lumen of one of the vessels being treated. The forward end 84 is retained within the vessel and urges the base 88 of the body open to ensure that the shoulder engages the wall of the vessel to prevent the device 80 from becoming dislodged from within the shunt.

As detailed above, in making a device of the invention it is desirable to attach the ends of the wire strands forming the metal fabric 10 to one another to prevent the fabric from unraveling. In the illustrations of FIGS. 6A–6C, a clamp 15 is used to tie together the ends of the wire strands adjacent the front end 84 of the device. It is to be understood that this clamp 15 is simply a schematic illustration, though, and that the ends could be attached in other ways, such as by welding, soldering, brazing, use of a biocompatible cementitious material or in any other suitable fashion.

The rearward ends of the wire strands are shown as being attached to one another by an alternative clamping means 90. This clamp 90 serves the same purpose as the schematically illustrated clamp 15, namely to interconnect the ends of the wires. However the clamp 90 also serves to connect the device 80 to a delivery system (not shown). In the embodiment shown, the clamp 90 is generally cylindrical in shape and has a recess for receiving the ends of the wires to substantially prevent the wires from moving relative to one another, and a threaded outer surface. The threaded outer surface is adapted to be received within a cylindrical recess (not shown) on a distal end of a delivery device and to engage the threaded inner surface of the delivery device's recess.

The delivery device (not shown) can take any suitable shape, but desirably comprises an elongate, flexible metal shaft having such a recess at its distal end. The delivery device can be used to urge the PDA occlusion device 80 through the lumen of a catheter for deployment in a channel of the patient's body, as outlined below. When the device is deployed out the distal end of the catheter, the device will still be retained by the delivery device. Once the proper position of the device 80 in the shunt is confirmed, the shaft of the delivery device can be rotated about its axis to unscrew the clamp 90 from the recess in the delivery means.

By keeping the PDA device 80 attached to the delivery means, the operator could still retract the device for repositioning if it is determined that the device is not properly positioned in the first attempt. This threaded attachment will also allow the operator to control the manner in which the device 80 is deployed out of the distal end of the catheter. As explained below, when the device exits the catheter it will tend to resiliently return to a preferred expanded shape which is set when the fabric is heat treated. When the device springs back into this shape, it may tend to act against the distal end of the catheter, effectively urging itself forward beyond the end of the catheter. This spring action could conceivably result in improper positioning of the device if the location of the device within a channel is critical, such as where it is being positioned in a shunt between two vessels. Since the threaded clamp 90 can enable the operator to maintain a hold on the device during deployment, the spring action of the device can be controlled and the operator can control the deployment to ensure proper positioning.

Figure 7:
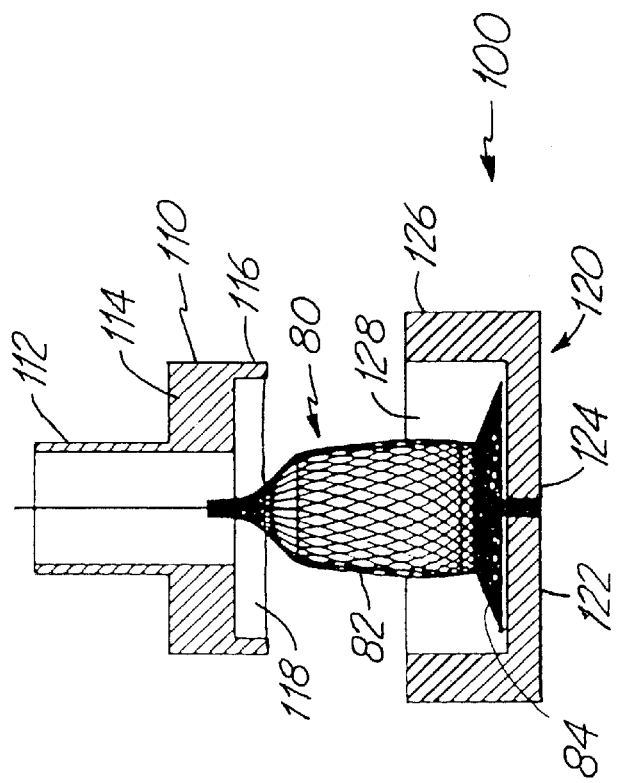
FIG. 7 is a side, cross sectional view of a molding element suitable for forming the medical device shown in FIGS. 6A–6C.

A PDA occlusion device 80 of this embodiment of the invention can advantageously be made in accordance with the method outlined above, namely deforming a metal fabric to generally conform to a molding surface of a molding element and heat treating the fabric to substantially set the fabric in its deformed state. FIG. 7 shows a molding element 100 which may be suitable for forming a PDA occlusion device 80 such as that shown in FIGS. 6A–6C.

The molding element 100 generally comprises a body portion 110 and an end plate 120. The body portion 110 is adapted to receive and form the body 82 of the device 80 while the end plate is adapted to compress against the metal fabric to form the forward end 84. The body portion 110 includes an elongate, generally tubular central segment 112 which is sized to receive the elongate body 82 of the device. The central segment 112 of the molding element 100 optimally has an internal diameter slightly less than the natural, relaxed outer diameter of the tubular braid of which the device is formed. This compression of the braid will help yield devices with reproducibly sized bodies 82. The forward end of the body portion 110 includes a back plate 114 which has a generally annular sidewall 116 depending downwardly therefrom. The sidewall defines a recess 118 which is generally circular in shape.

The end plate 120 of the molding element 100 has a generally disc-shaped face 122, which desirably has a clamp port 124 approximately centered therein for receiving a clamp 15 attached to the metal fabric, as noted above. The end plate also has an annular sidewall 126 which extends generally upwardly from the face 122 to define a generally cylindrical recess 128 in the end plate 120. The sidewall 116 of the body portion 110 is sized to be received within the recess 128 of the end plate.

In use, the metal fabric is placed in the molding element and the body portion 110 and the end plate 120 are brought toward one another. The inner face of the back plate 114 will engage the fabric and tend to urge it under compression generally radially outwardly. The fabric will then be enclosed generally within the recess 118 of the body portion and will generally conform to the inner surface of that recess. If one prevents the entire clamp 15 from passing through the clamp port 124, the fabric will be spaced slightly away from the inner surface of the face 122, yielding a slight dome shape in the forward end 84 of the device, as illustrated in FIGS. 6. Although the illustrated embodiment includes such a dome-shaped forward end, it is to be understood that the forward end may be substantially flat (except for the clamp 15), which can be accomplished by allowing the clamp to be received entirely within the clamp port 124 in the end plate.

Once the fabric is compressed in the molding element 100 so that it generally conforms to the molding surface of the molding element, the fabric can be subjected to a heat treatment such as is outlined above. When the molding element is opened again by moving the body portion 110 and the end plate 120 away from one another again, the fabric will generally retain its deformed, compressed configuration. The device can then be collapsed, such as by urging the clamps 15, 90 generally axially away from one another, which will tend to collapse the device toward its axis. The collapsed device 80 can then be passed through a catheter for deployment in a channel in a patient's vascular system.

Figure 8:
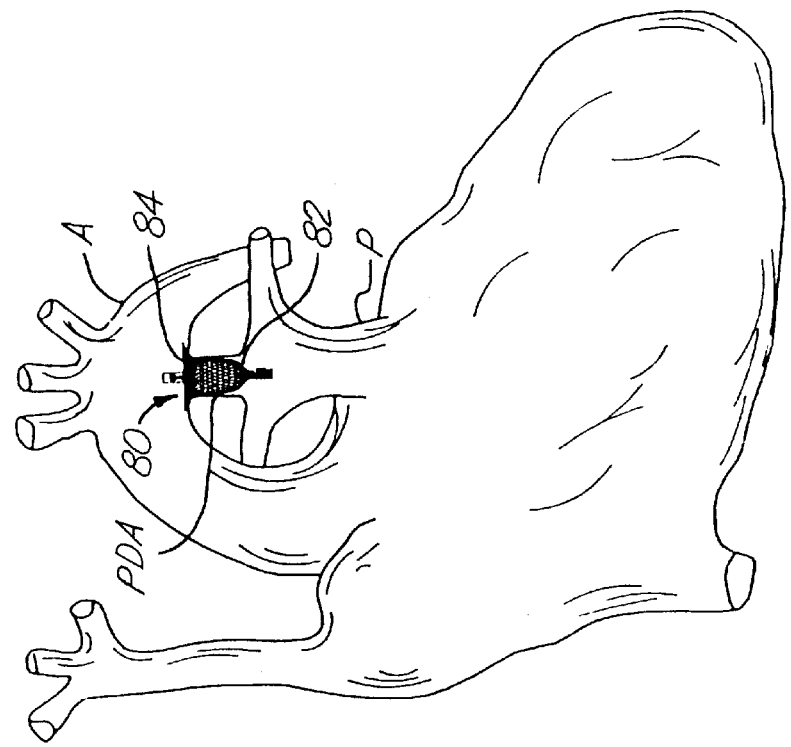
FIG. 8 is a schematic illustration showing the device of FIGS. 6A–6C deployed in a channel of a patient's vascular system to occlude a Patent Ductus Arteriosus.

FIG. 8 schematically illustrates how a medical device 80 generally as outlined above can be used to occlude a patent ductus arteriosus. In this case, there is a shunt, referred to as a PDA above, which extends between a patient's aorta A and the pulmonary artery P. The device 80 can be passed through the PDA, such as by keeping the device collapsed within a catheter (not shown), and the forward end 84 of the device can be allowed to elastically expand to substantially recover its thermally set, "remembered" shape from the heat treatment process, such as by urging the device distally to extend beyond the distal end of the catheter. This forward end 84 should be larger than the lumen of the shunt of the PDA.

The device can then be retracted so that the forward end 84 engages the wall of the pulmonary artery P. If one continues to retract the catheter, the engagement of the device with the wall of the pulmonary artery will tend to naturally pull the body portion 82 of the device from the catheter, which will permit the body portion to return to its expanded configuration. The body portion should be sized so that it will frictionally engage the lumen of the PDA's shunt. The device 80 will then be held in place by the combination of the friction between the body portion and the lumen of the shunt and the engagement between the wall of the pulmonary artery and the forward end 84 of the device. Over a relatively short period of time, thrombi will form in and on the device 80 and the thrombi will occlude the PDA. If so desired, the device may be coated with a suitable thrombolytic agent to speed up the occlusion of the PDA.

FIGS. 9A and 9B are a side view and an end view, respectively, of yet another embodiment of the present invention. This device 180 can be used for a variety of applications in a patient's blood vessels. For example, if a fabric having a relatively high pick (i.e. where the wire density is fairly great) is used in making the device, the device can be used to occlude blood vessels. In other applications, it may serve as a filter within a channel of a patient's body, either in a blood vessel or in another channel, such as in a urinary tract or biliary duct. In order to further enhance or reduce the device's tendency to occlude the vessel, depending on the application of the device a suitable known thrombogenic or antithrombogenic coating may be applied to the device.

This filter 180 has a generally conical configuration, tapering generally radially outwardly from its rearward end 182 to its forward end 184. A length of the device adjacent its forward end is adapted to engage the walls of a lumen of a channel. The maximum diameter of the filter device 180 is therefore at least as large as the inner diameter of the channel in which it is to be positioned so that at least the forward end will engage the wall of the vessel to substantially lock the device in place.

Having a series of unsecured ends 185 of the wire strands adjacent the forward end of the device will assist in seating the device in the channel because the ends of the wires will tend to dig into the vessel wall slightly as the forward end of the device urges itself toward its fully expanded configuration within the vessel. The combination of the friction between the outwardly urging forward end of the device and the tendency of the wire ends to dig into the vessel walls will help ensure that the device remains in place where it is deployed rather than floating freely within a vessel to reach an undesired location.

The method in which the device 180 of the invention is deployed may vary depending on the nature of the physiological condition to be treated. For example, in treating an arterio-venous fistula, the device may be carefully positioned, as described above, to occlude the flow of blood at a fairly specific location. In treating other conditions (e.g. an arterio-venous malformation), however, if may be desired to simply release a number of these devices upstream of the malformation in a vessel having a larger lumen and simply allow the devices to drift from the treatment site to lodge in smaller vessels downstream.

The decision as to whether the device 180 should be precisely positioned at an exact location within the channel in a patient's body or whether it is more desirable to allow the device(s) to float to their final lodging site will depend on the size of the channels involved and the specific condition to be treated. This decision should be left to the individual operator to be made on a case-by-case basis as his or her experience dictates; there is no one right or wrong way to deploy the device 180 without regard to the conditions at hand.

In the embodiment shown in FIGS. 9A and 9B, the wall of the device extends generally linearly from a position adjacent the clamp 90 and the other end of the device, approximating a conical shape. Due to the presence of the clamp 90, though, the end of the device immediately adjacent the clamp may deviate slightly from the cone shape, as indicated in the drawings. Alternatively, the wall may be curved so that the diameter of the device changes more rapidly adjacent the rearward end than it does adjacent its forward end, having an appearance more like a rotation of a parabola about its major axis than a true cone. Either of these embodiments should suffice in occluding a vessel with the device 180, such as to occlude a vessel.

The ends of the wire strands at the rearward end 182 of the device are secured with respect to one another, such as by means of a threaded clamp 90 such as that described above in connection with FIGS. 6A–6C. Portions of the wire strands adjacent the forward end 184 may also be secured against relative movement, such as by spot welding wires to one another where they cross adjacent the forward end. Such a spot weld is schematically illustrated at 186 in FIGS. 9A and 9B.

In the embodiment illustrated in FIGS. 9, though, the ends of the wire strands adjacent the forward end 184 in the finished device need not be affixed to one another in any fashion. These strands are held in a fixed position during the forming process to prevent the metal fabric from unraveling before it is made into a finished device. While the ends of the wire strands adjacent the forward end remain fixed relative to one another, they can be heat treated, as outlined above. The heat treatment will tend to fix the shapes of the wires in their deformed configuration wherein the device generally conforms to a molding surface of the molding element. When the device is removed from contact with the molding element, the wires will retain their shape and tend to remain intertwined. Accordingly, when the device is released from contact with the molding element, even if the ends of the wires are released from any constraint the device should still substantially retain its shape.

Figure 10B:
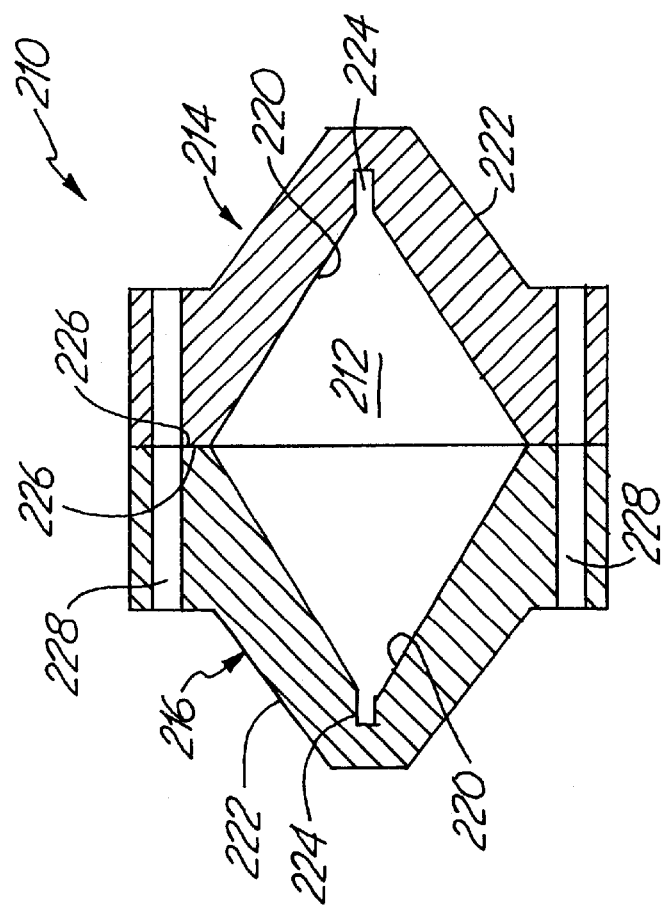
FIG. 10B is a cross-sectional view of another molding element suitable for forming the invention of FIGS. 9A and 9B.
Figure 10A:
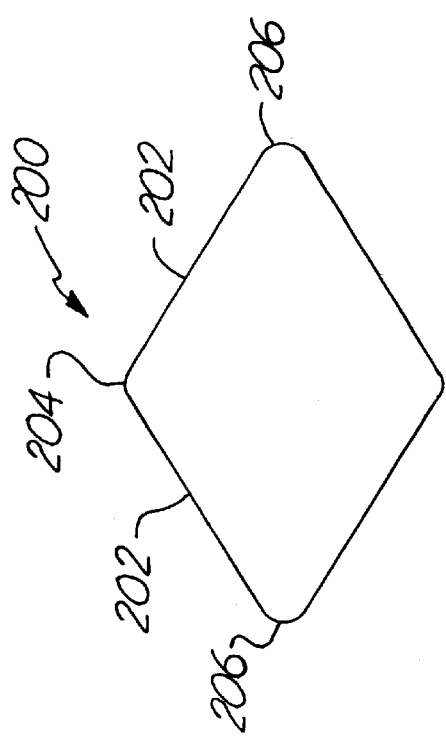
FIG. 10A is a side view of one molding element suitable for forming the invention of FIGS. 9A and 9B.
Figure 10:
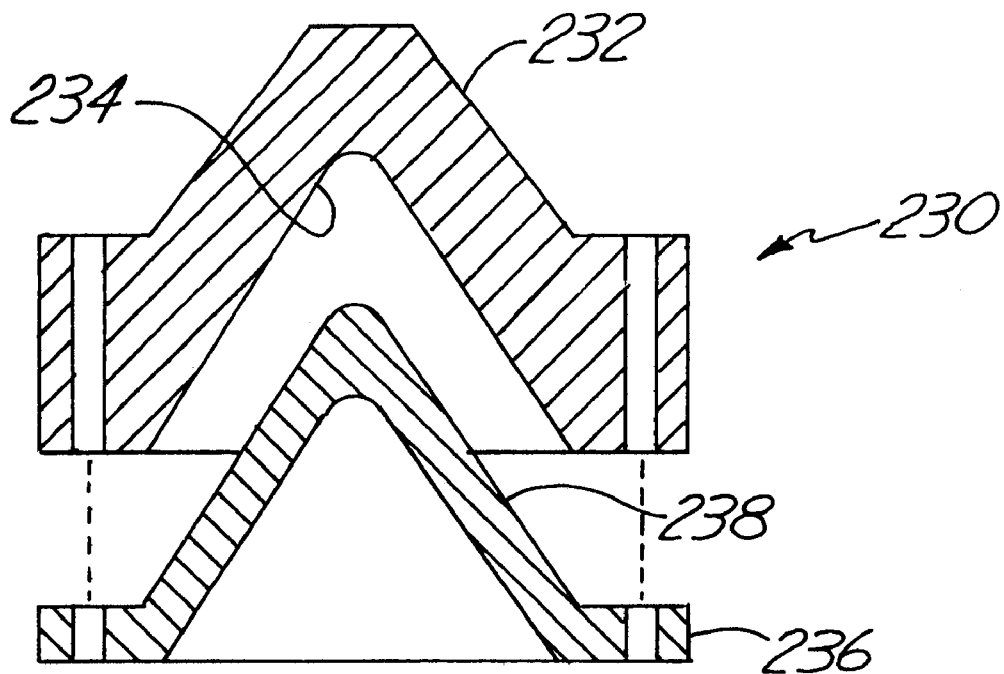
FIG. 10C is a cross-sectional view of still another molding element suitable for forming the invention of FIGS. 9A and 9B.

FIGS. 10A–10C illustrate three suitable molds for use in forming the filter 180 of FIGS. 9A and 9B. In FIG. 10A, the molding element 200 is a single piece which defines a pair of generally conical portions abutting one another. In another similar embodiment (not shown), the molding element 200 may be generally ovoid, shaped not unlike an American football or a rugby ball. In the embodiment illustrated in FIG. 10A, though, the molding element is a little bit less rounded. This molding element comprises two conical segments 202 which abut one another at their bases, defining a larger diameter at the middle 204 of the element which can taper relatively uniformly toward the ends 206 of the element 200.

When the a tubular braid is used in forming this device, the tubular metal fabric may be applied to the molding element by placing the molding element within the tubular braid and clamping the ends of the braid about the molding element before cutting the braid to the desired length. In order to better facilitate the attachment of the clamps 90 to the ends of the tubular braid, the ends 206 of the molding element may be rounded, as shown, rather than tapering to a sharper point at the ends of the molding element. In order to ensure that the braid more closely conforms to the outer surface of the molding element 200, i.e. the molding element's molding surface, the natural, relaxed diameter of the braid should be less than the maximum diameter of the element, which occurs at its middle 204. This will place the metal fabric in tension about the middle of the element and, in combination with the clamps at the ends of the braid, cause the braid to generally conform to the molding surface.

FIG. 10B illustrates an alternative molding element 210 for forming a device substantially as shown in FIGS. 9A and 9B. Whereas the molding element 200 is intended to be received within a recess in the metal fabric, such as within the lumen of a length of tubular braid, the molding element 210 has an internal cavity 212 adapted to receive the fabric. In this embodiment, the molding element may comprise a pair of molding sections 214, 216 and these mold sections may be substantially identical in shape. Each of the molding sections 214, 216 generally comprise a conical inner surface 220 defined by a wall 222. Each section also may be provided with a generally cylindrical axial recess 224 for receiving a clamp 15 (or 90) carried by an end of the metal fabric.

The two molding sections should be readily attached to one another with the larger, open ends 226 of the sections abutting one another. The mold sections can simply be clamped together, such as by providing a reusable jig (not shown) which can be used to properly position the sections 214, 216 with respect to one another. If so desired, bolt holes 228 or the like may be provided to allow a nut and bolt, or any similar attachment system, to be passed through the holes and attach the sections 214, 216 together.

In use, a suitably sized piece of a metal fabric, optimally a length of a tubular braid, is placed in the recess 212 of the molding element and the two molding sections 214, 216 are urged toward one another. The fabric should have a relaxed axial length longer than the axial length of the recess 212 so that bringing the sections toward one another will axially compress the fabric. This axial compression will tend to urge the wire strands of the braid radially outwardly away from the axis of the braid and toward engagement with the molding surface of the element 210, which is defined by the surface of the recess 212.

Once the metal fabric is deformed to generally conform to the molding surface of either molding element 200 or 210, the fabric can be heat treated to substantially set the shape of the fabric in its deformed state. If molding element 200 is used, it can then be removed from the interior of the metal fabric. If there is sufficient room between the resilient wire strands, the molding element can simply be removed by opening the web of wire strands and pulling the molding element out of the interior of the metal fabric. If molding element 210 is employed, the two molding sections 214, 216 can be moved away from one another and the molded fabric can be retrieved from the recess 212. Depending on the shape of the molding surface, the resulting formed shape may resemble either a pair of abutting hollow cones or, as noted above, a football, with clamps, welds or the like provided at either end of the shape.

This shape can then be cut into two halves by cutting the wires in a direction generally perpendicular to the shared axis of the cones (or the major axis of the ovoid shape) at a location about midway along its length. This will produce two separate filter devices 180 substantially as illustrated in FIGS. 9A and 9B. If the wires strands are to be joined adjacent the forward end of the device (such as by the weldments shown as 186 in FIGS. 9A and 9B), this can be done before the conical or ovoid shape is severed into two halves. Much the same net shape could be accomplished by cutting the metal fabric into halves while it is still carried about molding element 200. The separate halves having the desired shape could then be pulled apart from one another, leaving the molding element ready for forming additional devices.

In an alternative embodiment of this method, the molding element 200 is formed of a material selected to permit the molding element to be destroyed for removal from the interior of the metal fabric. For example, the molding element may be formed of a brittle or friable material, such as glass. Once the material has been heat treated in contact with the molding surface of the molding element, the molding element can be broken into smaller pieces which can be readily removed from within the metal fabric. If this material is glass, for example, the molding element and the metal fabric can be struck against a hard surface, causing the glass to shatter. The glass shards can then be removed from the enclosure of the metal fabric. The resultant shape can be used in its generally conical shape, or it can be cut into two separate halves to produce a device substantially as shown in FIGS. 9A and 9B.

Alternatively, the molding element 200 can be formed of a material which can be chemically dissolved, or otherwise broken down, by a chemical agent which will not substantially adversely affect the properties of the metal wire strands. For example, the molding element can be formed of a temperature-resistant plastic resin which is capable of being dissolved with a suitable organic solvent. The fabric and the molding element can be subjected to a heat treatment to substantially set the shape of the fabric in conformance with the surface of the molding element, whereupon the molding element and the metal fabric can be immersed in the solvent. Once the molding element is substantially dissolved, the metal fabric can be removed and either used in its current shape or cut into separate halves, as outlined above.

Care should be taken to ensure that the material selected to form the molding element is capable of withstanding the heat treatment without losing its shape, at least until the shape of the fabric has been set. For example, the molding element could be formed of a material having a melting point above the temperature necessary to set the shape of the wire strands, but below the melting point of the metal forming the strands. The molding element and metal fabric can then be heat treated to set the shape of the metal fabric, whereupon the temperature can be increased to substantially completely melt the molding element, thereby removing the molding element from within the metal fabric.

It should be understood that the methods outlined immediately above for removing the metal fabric 10 from the molding element 200 can be used in connection with other shapes, as well. Although these methods may not be necessary or desirable if the molding element is carried about the exterior of the metal fabric (such as are elements 30–40 of the molding element 20 of FIGS. 2–4), if the molding element or some portion thereof is enclosed within the formed metal fabric (such as the internal molding section of the molding element 20), these methods can be used to effectively remove the molding element without adversely affecting the medical device being formed.

FIG. 10C illustrates yet another molding element 230 which can be used in forming a medical device such as that illustrated in FIGS. 9A and 9B. This molding element comprises an outer molding section 232 defining a tapered inner surface 234 and an inner molding section 236 having an outer surface 238 substantially the same shape as the tapered inner surface 234 of the outer molding section. The inner molding section 236 should be sized to be received within the outer molding section, with a piece of the metal fabric (not shown) being disposed between the inner and outer molding sections. The molding surface of this molding element 230, to which the fabric will generally conform, can be considered to include both the inner surface 234 of the outer molding section and the outer surface 238 of the inner molding section.

This molding element 230 can be used with a metal fabric which is in the form of a tubular braid. If such a fabric is used and a clamp 15 (not shown in this drawing) or the like is provided to connect the ends of the wire strands adjacent one end of the device, a recess (not shown) analogous to the cavity 46 in the face of the compression disk 44 of molding element 20 (FIGS. 2–4) can be provided for receiving the clamp.

However, the present molding element 230 can be used quite readily with a flat woven piece of metal fabric, such as is illustrated in FIG. 1B. In using such a fabric, a suitably sized and shaped piece of fabric is cut; in using the molding element 230 to produce a device 180 analogous to that shown in FIGS. 9A and 9B, for example, a generally disk-shaped piece of the metal fabric 10' can be used. The metal fabric is then placed between the two sections 232, 236 of the molding element and the sections are moved together to deform the fabric therebetween. After heat treatment, the fabric can be removed and will retain substantially the same shape as it had when it was deformed between the two molding sections.

As can be seen by the discussion of the various molding elements 200, 210 and 230 in FIGS. 10A–10C, it should be clear that a number of different molding elements may achieve essentially the same desired shape. These molding elements may be received entirely within a closed segment of fabric and rely on tension and/or compression of the fabric to cause it to generally conform to the molding surface of the molding element, as with the element 200 of FIG. 10A. The molding element 210 of FIG. 10B substantially encloses the fabric within a recess in the mold and relies on compression of the fabric (in this case axial compression of a tubular braid) to deform the fabric to the desired configuration. Finally, the fabric may be compressed between two coacting parts of the molding element to deform the fabric, such as between the two sections 232, 236 of molding element 230 in FIG. 10C. Any one or more of these techniques may be used in achieving a finished product having a desired shape.

The method in accordance with the present invention further includes a method of treating a physiological condition of a patient. In accordance with this method, a medical device suitable for treating the condition, which may be substantially in accordance with one of the embodiments outlined above, is selected. For example, if a patent ductus arteriosus is to be treated, the PDA occlusion device 80 of FIGS. 6A–6C can be selected. Once the appropriate medical device is selected, a catheter may be positioned within a channel in patient's body to place the distal end of the catheter adjacent the desired treatment site, such as immediately adjacent (or even within) the shunt of the PDA.

Medical devices made in accordance with the method of the invention outlined above have a preset expanded configuration and a collapsed configuration which allows the device to be passed through a catheter. The expanded configuration is generally defined by the shape of the medical fabric when it is deformed to generally conform to the molding surface of the molding element. Heat treating the metal fabric substantially sets the shapes of the wire strands in the reoriented relative positions when the fabric conforms to the molding surface. When the metal fabric is then removed from the molding element, the fabric may define a medical device in its preset expanded configuration.

The medical device can be collapsed into its collapsed configuration and inserted into the lumen of the catheter. The collapsed configuration of the device may be of any shape suitable for easy passage through the lumen of a catheter and proper deployment out the distal end of the catheter. For example, the devices shown in FIGS. 5 may have a relatively elongated collapsed configuration wherein the devices are stretched along their axes. This collapsed configuration can be achieved simply by stretching the device generally along its axis, e.g. by manually grasping the clamps 15 and pulling them apart, which will tend to collapse the expanded diameter portions 64 of the device 60 inwardly toward the device's axis. The PDA occlusion device 80 of FIGS. 6 also operates in much the same fashion and can be collapsed into its collapsed configuration for insertion into the catheter by applying tension generally along the axis of the device. In this regard, these devices 60 and 80 are not unlike "Chinese handcuffs", which tend to constrict in diameter under axial tension.

Once the medical device is collapsed and inserted into the catheter, it may be urged along the lumen of the catheter toward the distal end of the catheter. This may be accomplished by using a guidewire or the like to abut against the device and urge it along the catheter. When the device begins to exit the distal end of the catheter, which is positioned adjacent the desired treatment site, it will tend to resiliently return substantially entirely to its preset expanded configuration. Superelastic alloys, such as nitinol, are particularly useful in this application because of their ability to readily return to a particular configuration after being elastically deformed to a great extent. Hence, simply urging the medical device out of the distal end of the catheter tend to properly deploy the device at the treatment site.

Although the device will tend to resiliently return to its initial expanded configuration (i.e. its shape prior to being collapsed for passage through the catheter), it should be understood that it may not always return entirely to that shape. For example, the device 60 of FIG. 5 is intended to have a maximum outer diameter in its expanded configuration at least as large as and preferably larger than, the inner diameter of the lumen in which it is to be deployed. If such a device is deployed in a vessel having a small lumen, the lumen will prevent the device from completely returning to its expanded configuration. Nonetheless, the device would be properly deployed because it would engage the inner wall of the lumen to seat the device therein, as detailed above.

If the device is to be used to permanently occlude a channel in the patient's body, such as the devices 60 and 80 described above may be, one can simply retract the catheter and remove it from the patient's body. This will leave the medical device deployed in the patient's vascular system so that it may occlude the blood vessel or other channel in the patient's body. In some circumstances, the medical device may be attached to a delivery system in such a manner as to secure the device to the end of the delivery means, such as when the threaded clamp 90 shown in FIGS. 6 and 9 are attached to a distal end of the delivery means, as explained above. Before removing the catheter in such a system, it may be necessary to detach the medical device from the delivery means before removing the catheter and the delivery means.

While a preferred embodiment of the present invention has been described, it should be understood that various changes, adaptations and modifications may be made therein without departing from the spirit of the invention and the scope of the appended claims.

What is claimed is:

1. A method of forming a medical device for deployment in a channel in a patient's body, the device having a preset expanded configuration and a collapsed configuration enabling passage of the device through a catheter, comprising the steps of:

a) providing a fabric formed of a plurality of strands having a first relative orientation with respect to one another, the strands being formed of a material which can be heat treated to substantially set a desired shape;

b) generally conforming the fabric to an internal surface of a molding element to substantially define the device's expanded configuration;

c) treating the fabric while conformed to the internal surface of the molding element to substantially set the strands in their expanded configuration; and d) removing the fabric from contact with the internal surface of the molding element, whereby the fabric defines a medical device which can be deformed into its collapsed configuration for passage through a catheter for deployment in a channel of a patient's body, and which substantially resumes its preset expanded configuration in such channel.

2. The method of claim 1, wherein the molding element comprises a plurality of mold sections, each mold section having an internal surface, the mold sections being assembled such that the internal surfaces of the mold sections together define the internal surface of the molding element.

3. The method of claim 2, wherein the mold sections are assembled about the fabric to substantially enclose the fabric within the molding element.

4. A method of forming a medical device for deployment in a channel in a patient's body, the device having a preset expanded configuration and a collapsed configuration enabling passage of the device through a catheter, comprising the steps of:

a) providing a fabric formed of a plurality of strands having a first relative orientation with respect to one another, said strands each having a proximal end and a distal end, and said strands being formed of a material which can be heat treated to substantially set a desired shape;

b) securing at least one of the proximal end and distal end of said strands at a common endpoint;

c) generally conforming the fabric to a molding element to substantially define a shape of an expanded configuration of the device;

d) treating the fabric while conformed to the molding element to substantially set the strands in the shape of the expanded configuration of the device; and e) removing the fabric from contact with the molding element, whereby the device formed thereby can be deformed into a collapsed configuration for passage through a catheter for deployment in a channel of a patient's body, and which substantially resumes the expanded configuration in such channel.

5. The method as recited in claim 4, further including attaching a clamp to an end of said strands secured at the common endpoint.

6. The method as recited in claim 5, wherein said clamp has a threaded bore adapted for rotationally receiving a delivery device.

7. The method as recited in claim 4, wherein after removing the fabric from contact with the molding element, further including the step of attaching an occluding fiber to said fabric.

8. The method as recited in claim 4, wherein the device is shaped to be suitable for use as a vascular trap.

9. The method as recited in claim 4, wherein the device is shaped to be suitable for use as a vascular graft.

10. The method as recited in claim 4, wherein the device is shaped to be suitable for use as a vascular plug.

11. The method as recited in claim 4, wherein the device is shaped to be suitable for use to occlude an atrial septal defect.

12. The method as recited in claim 4, wherein the device is shaped to be suitable for use to occlude a ventricular septal defect.

13. The method as recited in claim 4, wherein the device is shaped to be suitable for use to occlude a patent ductus arteriosus.

* * * * *